United States Patent [19]
Kohsaka et al.

[11] Patent Number: 5,604,319
[45] Date of Patent: Feb. 18, 1997

[54] SAMPLING DEVICE FOR GAS ANALYZERS

[75] Inventors: Hiroji Kohsaka; Satoshi Ohtsuki, both of Miyanohigashi-machi, Japan

[73] Assignee: Horiba, Ltd.,, Kyoto, Japan

[21] Appl. No.: 410,349

[22] Filed: Mar. 24, 1995

[30] Foreign Application Priority Data

Mar. 26, 1994 [JP] Japan .................... 6-079916

[51] Int. Cl.⁶ .................................... G01N 1/22
[52] U.S. Cl. .................. 73/863.11; 73/863.43; 73/863.514; 73/863.58; 73/863.81
[58] Field of Search .............. 73/23.31, 23.35, 73/863.01, 23.41, 863.02, 863.03, 863.11, 863.12, 863.58, 864.81, 864.73, 863.51, 863.43, 63.58, 863.71, 863.81–863.86

[56] References Cited

U.S. PATENT DOCUMENTS

| | | | |
|---|---|---|---|
| 3,699,814 | 10/1972 | Kaufman | 73/863.11 |
| 3,784,902 | 1/1974 | Huber | 73/863.03 |
| 3,996,008 | 12/1976 | Fine et al. | 73/23.35 |
| 4,317,379 | 3/1982 | Oberländer et al. | 73/863.83 |
| 4,383,839 | 5/1983 | Sisti et al. | 55/67 |
| 4,660,408 | 4/1987 | Lewis | 73/863.12 |
| 5,014,541 | 5/1991 | Sides et al. | 73/23.41 |
| 5,184,501 | 2/1993 | Lewis etal. | 73/863.01 |
| 5,337,595 | 8/1994 | Lewis | 73/23.31 |

*Primary Examiner*—Hezron E. Williams
*Assistant Examiner*—Nashmiya Ashraf
*Attorney, Agent, or Firm*—Poms, Smith, Lande & Rose

[57] ABSTRACT

A sampling device for a gas analyzer in which a constant-rate flow of diluted sample gas is sampled by a constant-volume sampling device. A gas inlet port of a sampling passage of the constant-volume sampling device is positioned in a throat portion of a main venturi tube, or slightly upstream or downstream of the throat portion. A cold trap is provided downstream of the sampling passage to collect and supply a portion of the sampled gas to be analyzed. The velocity of the diluted sample gas in the throat portion of the main venturi tube is approximately Mach one, so that the sampling thereof is unaffected by pressure or flow-rate changes elsewhere in the system.

12 Claims, 1 Drawing Sheet

SAMPLING DEVICE FOR GAS ANALYZERS

BACKGROUND OF THE INVENTION

1. Field of the Invention

The present invention relates to a sampling device for a gas analyzer and, more particularly, to such a sampling device which samples a gas at a constant rate.

2. Description of the Prior Art

Gas chromatography is a procedure for analyzing exhaust gas from an engine of, for example, an automobile. The procedure generally requires the exhaust gas to be diluted with air and then sampled at a constant rate by means of a constant-volume sampling device. There are several methods for sampling the diluted exhaust gas.

The bag method diverts a sample of the diluted exhaust gas into a tetrabag by means of the constant-volume sampling device. The sample is generally uniform in concentration. Although the bag method is relatively simple, it does, however, have disadvantages in that not only is it difficult to apply the method to high-boiling-point components and highly-absorbent substances, but also the results of the method are apt to be influenced by the background of the bag itself.

Another method for sampling the diluted exhaust gas is the batch method. In this method the constant-volume sampling device collects a sample of the diluted exhaust gas in an absorbent solution or material during a drive mode. Although the exhaust gas sample in the batch method is uniformly concentrated, this method is disadvantageous in not only that the concentrated exhaust gas sample requires treatment, such as extraction and heating, prior to analysis, but also that considerable skill and time are required to perform this procedure.

Yet another method for sampling the diluted exhaust gas is the continuous measuring method. In this method the constant-volume sampling device introduces the diluted exhaust gas into a gas sampling loop. The sample of diluted exhaust gas is then equilibrated to atmospheric pressure which is followed by the introduction of a carrier gas or the like for gas chromatography. Although this method is generally simple and accurate, a drawback of this method is that only an instantaneous measurement can be achieved during the sampling; therefore, analysis of the drive mode cannot be achieved.

Therefore, there remains an unfulfilled need in the art of gas chromatography for a sampling device which is able to sample a diluted exhaust gas without the numerous drawbacks mentioned above.

SUMMARY OF THE INVENTION

The present invention has been achieved in view of the above described matters, and it is an object of the present invention to provide a sampling device capable of sampling a gas, for example, the exhaust gas from an automobile, without being influenced by background interference or requiring troubling pretreatment in the case where the concentration of a sample gas momentarily changes.

In order to achieve the above object, a sampling device for a gas analyzer according to the present invention samples a constant-rate flow of diluted sample gas by means of a constant-volume sampling device. The sampling device is characterized in that a gas inlet port of a sampling passage of the constant-volume sampling device is positioned in a throat portion of a main venturi tube, or slightly upstream or downstream of the throat portion. A cold trap is provided downstream of the sampling passage to collect a portion of the sampled gas for analysis. The gas inlet port may be a small-sized drum-type venturi tube positioned either upstream or downstream of the throat portion of the main venturi tube.

The sampled gas in the sampling passage preferably flows therethrough at a constant rate. More specifically, in order to measure the volume of the sampled gas collected in the cold trap for analysis, the velocity of flow of the gas during the sampling is multiplied by the corresponding time. If the flow of the sampled gas is not constant, the instantaneous velocity of the flow of sampled gas must be measured to obtain the volume of the sampled gas.

However, as the flow of the gas through the main venturi tube is constant and preferably has a Mach number of one, by placing the gas inlet port in the throat portion of the main venturi tube, the flow rate of the sampled gas will always be constant. Moreover, even if the pressure and the rate of flow of the sampled gas changes in the sampling passage or in some other passage of the analyzer, this will not influence the flow rate at the gas inlet port, so that the sampling of gas can be stabilized.

Furthermore, in the embodiment where a small-sized drum-type venturi tube is positioned upstream or downstream from the throat portion of the main venturi tube, the rate of flow will also be Mach one in this small-sized venturi tube. Consequently, the sampling of gas can stabilized in the same manner as in the above-described case.

DETAILED DESCRIPTION OF THE PREFERRED EMBODIMENTS

Figure 1:
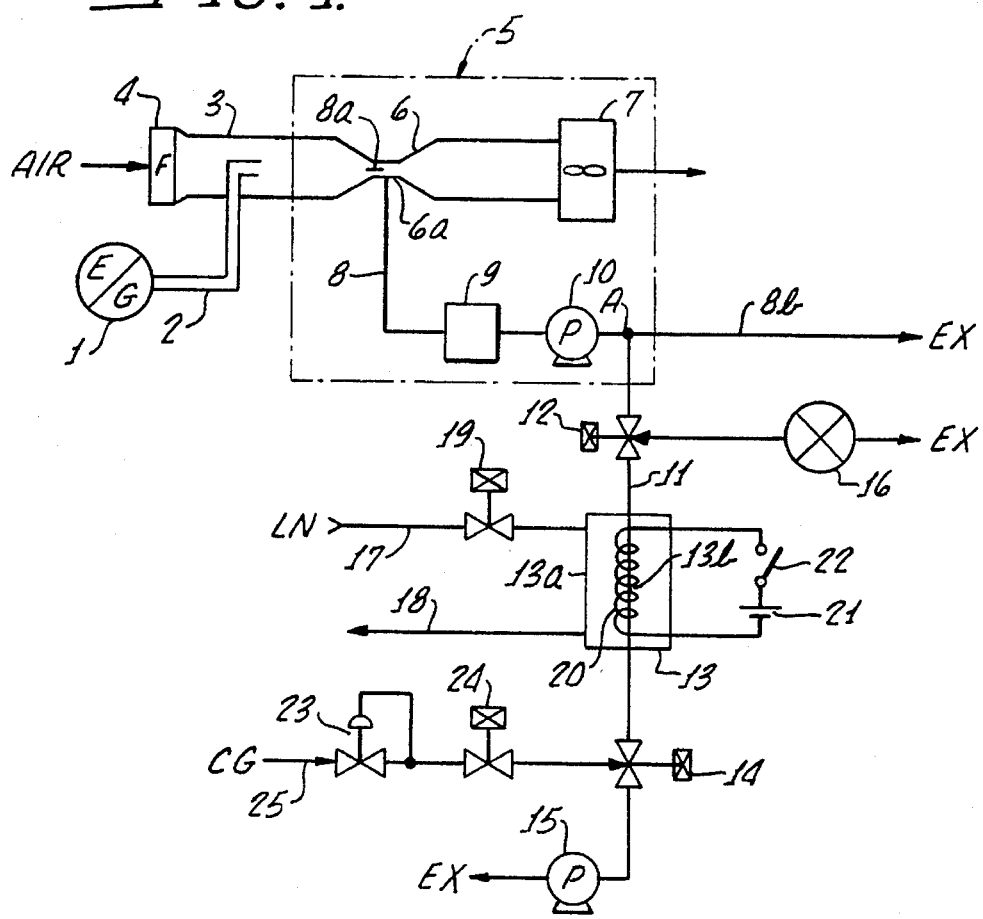
FIG. 1 is a schematic drawing showing a preferred embodiment of a sampling device according to the present invention.

Referring to FIG. 1, an exemplary embodiment of a sampling device according to the present invention is shown. An engine 1 of, for example, an automobile, is a source of exhaust gas. An exhaust pipe 2 communicates with the engine 1 and is connected with a dilution tunnel 3 on the downstream side thereof. An air filter 4 is provided upstream of the dilution tunnel 3 through which air is drawn into the dilution tunnel 3.

In addition, a constant-volume sampler (CVS) 5 is provided downstream of the dilution tunnel 3 and generally includes a main venturi tube 6, for example, a critical-flow venturi tube, with a throat portion 6a. A suction blower 7 is downstream of the main venturi tube 6 for drawing air through the dilution tunnel 3 and the main venturi tube 6 and for blowing the air to the outside of the system. Therefore, exhaust gas from the engine 1 is diluted with air being drawn through the filter 4 in the dilution tunnel 3, and the diluted exhaust gas is drawn through the main venturi tube 6 and blown out of the system by the suction blower 7. The throat portion 6a of the main venturi 6 may have an exemplary diameter of approximately 31 millimeters.

The CVS 5 further includes a sampling passage 8 branched from the throat portion 6a of the main venturi tube 6. The sampling passage 8 has a gas inlet port 8a at one end thereof and a bypass passage 8b at the other end thereof. The gas inlet port 8a is directed upstream in the throat portion 6a of the main venturi tube 6, and the bypass passage 8b provides an exhaust outlet for the sampling passage 8.

The CVS 5 further includes a filter 9 and a suction pump 10 disposed in-stream in the sampling passage 8. The filter 9 filters the sample of diluted exhaust gas in the sample passage 8 which is drawn therethrough by the suction pump 10. Therefore, the CVS 5 samples the diluted exhaust gas in the dilution tunnel 3 and provides the filtered sample of diluted exhaust gas at point A downstream of the suction pump 10 in the sampling passage 8.

A sample gas passage 11 is connected to the sampling passage 8 at point A. The sample gas passage 11 is provided in downstream order from point A a first three-way solenoid valve 12, a cold trap 13 with a jacket 13a and a trap tube 13b, a second three-way solenoid valve 14, and a suction pump 15. A hydrogen flame ionization detector (FID) 16 may be connected to the first solenoid valve 12.

The cold trap 13 may be provided a refrigerant-supplying passage 17 and a refrigerant-discharging passage 18 for supplying and discharging a refrigerant such as liquid nitrogen LN. The passages 17 and 18 are connected to the jacket 13a with the supplying passage 17 provided a two-way solenoid valve 19. Furthermore, the trap tube 13b, which is disposed inside the jacket 13a, is provide a heater 20 with a power source 21 and a switch 22.

The sample gas passage 11 is further provided means for supplying a carrier gas CG at the second solenoid valve 14 by means of a pressure regulator 23 and a two-way solenoid valve 24 positioned in-stream in a carrier gas-supplying passage 25.

The operation of the sampling device structurally described above will follow.

I. Sampling.

Exhaust gas from the engine 1 is introduced into the dilution tunnel 3 through the exhaust pipe 2. Diluting air passes through the filter 4 and flows through the dilution tunnel 3, thereby diluting the exhaust gas. A constant-rate flow of diluted exhaust gas is sampled by means of the CVS. 5. The sampled diluted exhaust gas ("the sample gas") flows into the gas inlet port 8A and into the sampling passage 8. As can be realized, the greater portion of the diluted exhaust gas flows toward the blower 7 and is exhausted out of the system.

A portion of the sample gas flowing through the sampling passage 8 is drawn into the sample gas passage 11 at point A by activating the pump 15. The sample gas flows through the cold trap 13, the second three-way solenoid valve 14 (which is open), and the pump 15, so that NOx, SOx, and the like present in the sample gas are exhausted out of the sample gas passage 11 downstream of the pump 15. At this time, the cold trap 13 is supplied with liquid nitrogen LN, so that appointed trapping can be achieved. Thus, a sample is collected in the cold trap 13.

II. Analysis.

After the collection of the sample, the three-way solenoid valves 12 and 14 are activated to close the gas sampling passage 11, and the two-way solenoid valve 24 is activated to open to supply the sample gas passage 11 with the carrier gas CG. Additionally, the heater 20 is activated by closing the switch 22, and the flow of liquid nitrogen LN is stopped. Accordingly, the sample gas collected in the cold trap 13 is quickly heated, thereby vaporizing the collected sample. The vaporized sample is then sent to the FID 16 via the first three-way solenoid valve 12, and the appointed analysis is conducted.

Although activating the pump 15 on and off and activating the solenoid valves 12 and 14 to open and close consequently causes changes in pressure and in flow rate of the sample gas in the sample gas passage 11 as described above, this does not effect or influence the flow rate of the diluted exhaust gas in the sampling passage 8 as the gas inlet port 8A is positioned in the throat portion 6a of the main venturi tube 6, through which the diluted exhaust gas flows preferably at approximately Mach one; therefore, the sampling of the diluted exhaust gas is stabilized. That is, as the main venturi tube 6 is a critical-flow venturi, the Mach number thereof is preferably one, and the flow therethrough is constant.

Figure 2:
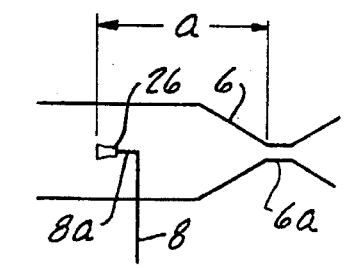
FIG. 2 is a schematic drawing showing the position of a gas inlet port in another preferred embodiment.

Referring to FIG. 2, the gas inlet port 8a of the sampling passage 8 does not need to be positioned in the throat portion 6a of the main venturi tube 6 but may be positioned, for example, slightly upstream of the throat portion 6a. As mentioned above, in order for the sampling of diluted exhaust gas not to be influenced by the pressure change and flow-rate change of the sample gas in the sample gas passage 11, the diluted exhaust gas at the gas inlet port 8a should be flowing preferably at Mach one. Therefore, if the gas inlet port 8a is positioned slightly upstream of the throat portion 6a of the main venturi tube 6, then a small-sized drum-type venturi tube 26 is provided at the gas inlet port 8a. Accordingly, a Mach number of one of the flow of the diluted exhaust gas is also achieved in the small-sized venturi tube 26. The small-sized venturi tube 26 may have a diameter of approximately one millimeter. Consequently, the stabilized sampling of the diluted exhaust gas can be achieved also in this embodiment. Further, it is preferable that the distance between the small-sized venturi tube 26 and the throat portion 26, as indicated by a, is less than approximately 100 millimeters.

As described above, in the case where the sampling is conducted by means of the small-sized venturi tube 26, if the airflow velocity of the diluted exhaust gas immediately upstream of the small-sized venturi tube 26 is Mach one (i.e., the Mach number of the small-sized venturi tube 26 is one), then the gas can be always sampled at a constant flow rate. Additionally, the small-sized venturi tube 26 may be provided slightly downstream of the throat portion 6a of the main venturi tube 6.

Figure 3:
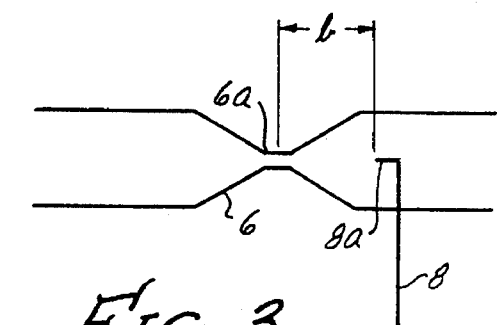
FIG. 3 is a schematic drawing showing the position of the gas inlet port in yet another preferred embodiment.

With reference to FIG. 3, the gas inlet port 8a of the sampling passage 8 is shown positioned downstream of the throat portion 6a. In this exemplary embodiment, no additional venturi tube is needed as the flow rate of the diluted exhaust gas through the throat portion 6a upstream of the gas inlet port 8a is Mach one. However, the distance from the gas inlet port 8a and the throat portion 6a, as indicated by b, should be preferably less than approximately 20 millimeters.

Furthermore, although the exhaust gas from automobiles was sampled in the above-described preferred embodiments, the present invention is not limited to automobiles but can be widely applied to other gas analyses.

As above described, according to the present invention, no tetrabag or the like is required, so that the operation is simplified, the speed is increased, there is no background influence, and the flow rate of the sampled gas is constant; therefore, the flow rate of sampled gas can be simply measured. Moreover, as shown in the preferred embodiments, in the case where the sampling device according to the present invention is combined with the gas chromatography, a large effect can be exhibited.

What is claimed is:

1. A sampling device for gas analyzers, comprising:
   a sample gas-conducting main venturi tube having a narrowed central portion including a constant gas flow rate-inducing throat portion;
   a sampling passage having an inlet port at a first end thereof and an outlet port at a second end thereof, said inlet port positioned within said central portion for obtaining a diluted gas at a constant rate; and
   a sample gas passage connected to said sampling passage downstream of said inlet port, said sample gas passage being provided in downstream order from said sampling passage, said sample gas passage including:
   a first three-way valve connected to a gas analyzer;
   a cold trap for collecting a sample of the diluted gas;
   a second three-way valve for selectively supplying a carrier gas to said sample gas passage; and
   a pump for drawing a portion of the diluted gas into said sample gas passage when activated;
   said cold trap having supply passage for selectively supplying a cryogen to said cold trap and a discharging passage for discharging the cryogen from said cold trap;
   said first and second three-way valves being actuatable such that the sample of the diluted gas collected by said cold trap is provided to the gas analyzer by the carrier gas.

2. A sampling device as claimed in claim 1, wherein said inlet port is positioned within said throat portion.

3. A sampling device as claimed in claim 1, wherein said inlet port is positioned downstream of said throat portion.

4. A sampling device as claimed in claim 1, further comprising a secondary venturi tube provided at said inlet port.

5. A sampling device as claimed in claim 4, wherein said secondary venturi tube is positioned upstream of said throat portion.

6. A sampling device as claimed in claim 4, wherein said secondary venturi tube is a drum-type venturi tube.

7. A sampling device as claimed in claim 4, wherein said secondary venturi tube is substantially smaller than said main venturi tube.

8. A sampling device as claimed in claim 1, wherein said main venturi tube is a critical-flow venturi tube.

9. A sampling device as claimed in claim 1, wherein the rate of flow of the diluted gas flowing through said main venturi tube is Mach one.

10. A sampling device as claimed in claim 1, wherein said cold trap further comprises:
    a refrigeration assembly and a heater assembly, said refrigeration assembly being connected to said supplying passage and said discharging passage, said refrigeration assembly being active when a portion of the diluted gas is flowing in said sample gas passage to trap said sample, said heater assembly being active when said refrigeration assembly is inactive to vaporize said sample; and
    a carrier assembly communicating with said sample gas passage via said second three-way valve and providing said carrier gas to said cold trap when said sample is vaporized to carry said sample to the gas analyzer.

11. A sampling device as claimed in claim 1, further comprising a suction pump positioned in said sampling passage between said inlet port and said cold trap.

12. A sampling device as claimed in claim 1, further comprising:
    a dilution tunnel positioned upstream of said main venturi tube for diluting a gas to be analyzed with air; and
    a suction fan position downstream of said main venturi tube.

* * * * *

UNITED STATES PATENT AND TRADEMARK OFFICE
CERTIFICATE OF CORRECTION

PATENT NO.    : 5,604,319
DATED         : February 18, 1997
INVENTOR(S)   : Hiroji Kohsaka; Satoshi Ohtsuki It is certified that error appears in the above-indentified patent and that said Letters Patent is hereby corrected as shown below:

Column 5, line 23, between "having" and "supply" insert --a--.

Signed and Sealed this

Sixth Day of May, 1997

Attest:

BRUCE LEHMAN

*Attesting Officer*    *Commissioner of Patents and Trademarks*